United States Patent [19]

Green et al.

[11] Patent Number: 5,583,034

[45] Date of Patent: Dec. 10, 1996

[54] ENHANCEMENT OF ADOPTOSIS USING ANTISENSE OLIGONUCLEOTIDES

[75] Inventors: Douglas R. Green, San Diego, Calif.; Thomas G. Cotter, Co. Kildare, Ireland

[73] Assignee: La Jolla Institute for Allergy and Immunology, La Jolla, Calif.

[21] Appl. No.: 200,723

[22] Filed: Feb. 22, 1994

[51] Int. Cl.$^6$ .............................. C12N 5/10; C12N 5/08; C07H 21/04; C12Q 1/68
[52] U.S. Cl. ........................ 435/240.2; 536/24.5; 435/6
[58] Field of Search ............................ 514/44; 536/24.5; 435/7.21, 7.23, 7.24, 6, 240.2

[56] References Cited

U.S. PATENT DOCUMENTS 5,360,893  11/1994  Owens et al. ............................ 530/350

FOREIGN PATENT DOCUMENTS 9222303  12/1992  WIPO ............................ A61K 31/70

OTHER PUBLICATIONS

J. Holt et al. Mol. Cell. Biol., vol. 8, #2 (Feb. 1988) pp. 963–973.
E. Uhlmann et al. Chemical Reviews, vol. 90, #4 (Jun. '90) pp. 543–584.
M. Cooney et al. Science, vol. 241 (Jul. 22, 1988) pp. 456–459.
C. Hélène et al, Biochimie, vol. 67 ('85) pp. 777–783.
S. Wu-Pong, Pharm. Tech., (Oct. 1994) pp. 102–114.
B. Tseng et al. Cancer Gene Therapy, vol. 1, #1 (Mar. 1994) pp. 65–71.
C. Stein et al. Science, vol. 261 (Aug. 20, 1993) pp. 1004–1012.
R. Weiss, Science News, vol. 139 (Feb. 16, 1991) pp. 108–109.
Y.–Y. Chen et al. PNAS, vol. 89 (Aug. 1992) pp. 6683–6687.
E. Wickstrom et al. FASEB J., vol. 5, #5 (Mar. 15, 1991) p. A1443.
J. Marx, Science, vol. 259 (Feb. 5, 1993) pp. 760–761.
C. Szczylik et al. Science, vol. 253 (Aug. 2, 1991) pp. 562–565.
A. Mes–Masson et al. PNAS, vol. 83 (Dec. 1986) pp. 9768–9772.
T. Smetsers et al. Leukemia, vol. 8, #1 (Jan. '94) pp. 129–140.
T. Skorski et al. J. Clin. Invent., vol. 92 (Jul. '93) pp. 194–202.
D. Tidd, Anticancer Research, vol. 10 ('90) pp. 1169–1182.
B. Monia et al. J. Biol. Chem., vol. 267, #28 (Oct. 5, 1992) pp. 19954–19962.
P. Westermann et al. Biomed. Biochim. Acta, vol. 48, #1 ('89) pp. 85–93.
W. James, Antiviral Chem. & Chemotherapy, vol. 2, #4 ('91) pp. 191–214.

*Primary Examiner*—Charles C. P. Rories
*Attorney, Agent, or Firm*—Fish & Richardson

[57] ABSTRACT

A method is disclosed for enhancement of the efficacy of therapeutic treatment for inducing cell death in a cell having an anti-apoptotic gene by the enhancement of apoptosis. An antisense oligonucleotide is disclosed which hybridizes with the nucleic acid sequence of the anti-apoptotic gene. The oligonucleotide is administered to the cell in an amount sufficient to inhibit expression of the gene, thus rendering the cell susceptible to induction of apoptosis, and consequently achieving higher efficacy of therapeutic treatment.

14 Claims, 11 Drawing Sheets

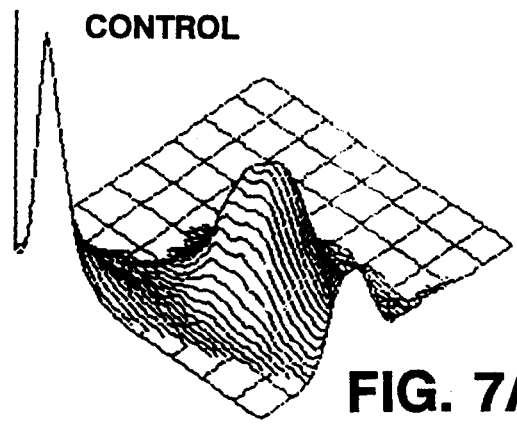
FIG. 7A CONTROL
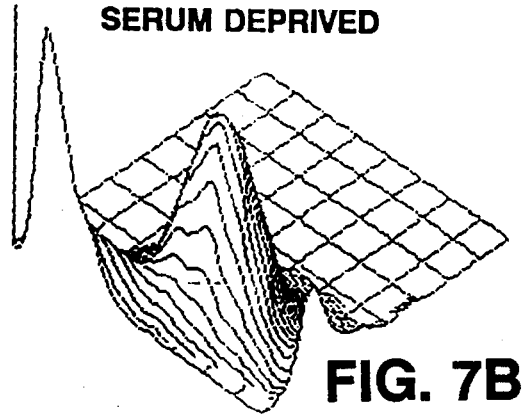
FIG. 7B SERUM DEPRIVED
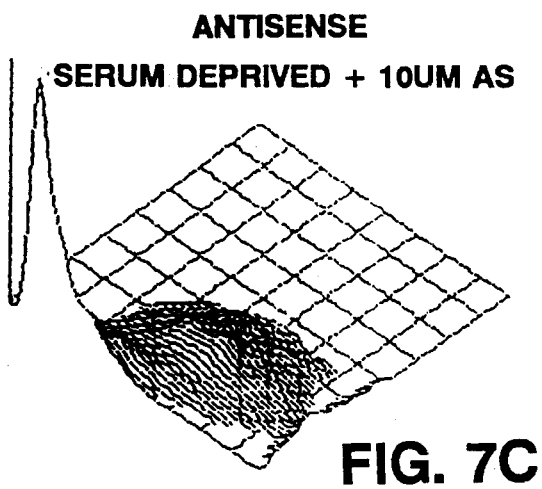
FIG. 7C ANTISENSE SERUM DEPRIVED + 10UM AS
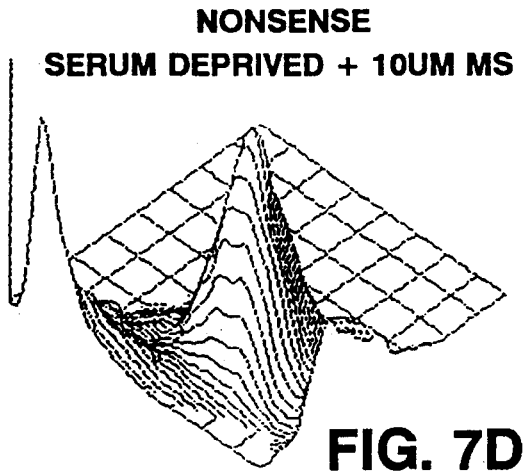
FIG. 7D NONSENSE SERUM DEPRIVED + 10UM MS

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:1:

```
ATGGTGGACC CGGTGGGC                                                    18
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:2:

```
GCCCTTCAGC GGCCAGTA                                                    18
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: AS-bcr-abl ( i x ) FEATURE:
        ( A ) NAME/KEY: CDS
        ( B ) LOCATION: 1..18

( x i ) SEQUENCE DESCRIPTION: SEQ ID NO:3:

```
GCCCACCGGG TCCACCAT                                                    18
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: AS-abl ( i x ) FEATURE:
        ( A ) NAME/KEY: CDS
        ( B ) LOCATION: 1..18

( x i ) SEQUENCE DESCRIPTION: SEQ ID NO:4:

TACTGGCCGC TGAAGGGC                                                      18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: NS-bcr-abl 1

( i x ) FEATURE:
        ( A ) NAME/KEY: CDS
        ( B ) LOCATION: 1..18

( x i ) SEQUENCE DESCRIPTION: SEQ ID NO:5:

CGCGCCTCGT CCCAAGCA                                                      18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: NS-bcr-abl 2

( i x ) FEATURE:
        ( A ) NAME/KEY: CDS
        ( B ) LOCATION: 1..18

( x i ) SEQUENCE DESCRIPTION: SEQ ID NO:6:

CGCCCTCGTT CCCAAGCA                                                      18

ENHANCEMENT OF ADOPTOSIS USING ANTISENSE OLIGONUCLEOTIDES

This invention was made with government support under Grant No. 5 R01 AI-31591 awarded by the National Institutes of Health. The government has certain rights in this invention.

BACKGROUND OF THE INVENTION

1. Field of the Invention

This invention relates generally to antisense oligonucleotides and specifically to the enhancement of cell death by treatment of the cell with an antisense oligonucleotide specific for an anti-apoptotic gene in combination with a therapeutic means for induction of cell death.

2. Background of the Prior Art

Apoptosis is a form of cell death in which the cell actively participates in its own demise. Apoptosis is defined predominantly by morphological criteria. The characteristic features of apoptosis include cell shrinkage, chromatin condensation, and DNA fragmentation into oligonucleosomal ladder size units. Finally, fragments of the dying cell form sealed vesicles called apoptotic bodies which are rapidly removed by neighboring cells (Wylie, et al., *Int. Rev. Cytol.*, 68:251, 1980).

Most approaches to cancer therapy result in activation of apoptotic pathways. For example, apoptosis is the major form of cell death associated with the action of chemotherapeutic agents on tumor cells. Expression of genes that interfere with apoptosis can have important consequences for the efficacy of therapeutic approaches. In certain circumstances, drug resistance in cancer cells is actually due to resistance to apoptosis in general. Therefore, an antiapoptotic signal might provide such resistance to therapeutic approaches aimed at inducing cell death. For example, the expression of the bcl-2 gene in tumor cells has been shown to increase the resistance of cells to cytotoxic agents (Lozzio, et al., *Blood*, 45:321, 1975). It would be highly desirable to develop a method to identify those genes that interfere with apoptosis in order to regulate the expression of those genes such that the cells would become more susceptible to the induction of apoptosis and, therefore, enhance the efficacy of therapeutic treatment of the cells.

Resistance to chemotherapeutic treatment has been observed in chronic myelogenous leukemia (CML) cells. CML is characterized cytologically by the Philadelphia (Ph) chromosome, which results from the translocation of the c-abl gene on chromosome 9 to the bcr gene on chromosome 22. The result of this translocation is the expression of a bcr-abl fusion protein. Despite the fact that the function of the bcr-abl fusion protein has been studied by different groups, drug resistance of the CML patient to chemotherapeutic treatment remains an unsolved problem. Szczylik, et al., (*Science*, 253:562, 1991) recently indicated that antisense oligonucleotides to the bcr-abl breakpoint junction inhibited cell proliferation in patient-derived CML cells, and suggested using such antisense alone to treat CML patients. More recently, Szczylik, et al., (*J. Clin. Invest.* 92:194, 1993) also showed that treatment of Philadelphia leukemic cells, mixed 1:1 with normal bone marrow cells, with a combination of a low dose of mafosfamide and antisense to the bcr-abl breakpoint junction, was effective in killing the leukemic cells while sparing a high number of the normal cells and at least part of the abl sequence. The authors also emphasized the importance of not including antisense to the bcr region in order to avoid perceived deleterious side effects. However, based on this therapeutic approach, therapeutic antisense oligonucleotides would have to be individually designed in order to be effective, since the breakpoint junction between bcr and abl appears to vary from patient to patient.

Therefore, there is a need to develop a generalized method for inducing apoptosis in a cell having a bcr-abl translocation which avoids the necessity of determining a patient's particular bcr-abl breakpoint nucleotide sequence in order to develop an effective therapeutic agent. The present invention provides such a method and therapeutic agents.

SUMMARY OF THE INVENTION

The invention is based on the discovery that the use of antisense oligonucleotides which correspond to an anti-apoptotic gene of a cell, in conjunction with therapeutic treatment for inducing cell death, can enhance the efficacy of the therapeutic treatment of the cell through the inhibition of the expression of the anti-apoptotic gene.

One aspect of the invention provides an antisense oligonucleotide which hybridizes to the nucleic acid sequence of an anti-apoptotic gene and inhibits the expression of the gene. In a preferred embodiment, the antisense oligonucleotide is complementary to the translation start nucleic acid sequence of an anti-apoptotic gene such as bcr-abl. Pharmaceutical compositions comprising the antisense oligonucleotide and an acceptable carrier are also provided.

Another aspect of the present invention provides a method for inducing cell death in a cell having an anti-apoptotic gene, thereby enhancing the efficacy of therapeutic treatment. An antisense oligonucleotide hybridizing to the nucleic acid sequence of the anti-apoptotic gene is administered to the cell in an amount sufficient to inhibit the expression of the gene. Following antisense treatment, the cell is exposed to a therapeutic means for induction of cell death. In a preferred embodiment, an antisense oligonucleotide hybridizing to the translation start nucleic acid sequence of the anti-apoptotic gene is used to inhibit the expression of the anti-apoptotic gene.

Yet another aspect of the invention provides a method for identifying an antiapoptotic gene in a cell. Typically, such a cell should be resistant to induction of apoptosis. An antisense oligonucleotide which hybridizes to a nucleic acid sequence of a gene is administered to a cell having such an anti-apoptotic gene, in an amount sufficient to inhibit the expression of the gene. The cell is then exposed to a condition, such as a chemotherapeutic agent, which induces apoptosis in a cell now susceptible to the induction of apoptosis. The induction of apoptosis can then be detected in the cell by various methods. Cells which hybridize to the antisense would be susceptible to therapy according to the invention.

In a further embodiment, the invention provides a method for identification of an apoptotic agent by treating a cell with an antisense oligonucleotide which hybridizes to a known anti-apoptotic gene and the potential or candidate apoptotic agent and observing the effect on the cell.

The invention is defined in its fullest scope in the appended claims and is described below in its preferred embodiments.

DESCRIPTION OF THE DRAWINGS

FIG. 1A shows Nomarski and B) fluorescent images of AS-bcr-abl treated cells; FIG. 1C shows Nomarski and D) fluorescent images of NS-bcr-abl treated cells.

FIG. 7 is a FACScan Flow cytometer analysis showing the effect of oligonucleotide on bcr-abl expression in control and serum deprived K562 cells. The diagram shows ungated data for forward light scatter (x-axis) versus side light scatter (y-axis).

FIGS. 9A and 9B show control cells at 32° C. and 37° C.; 9C and 9D show NS-bcr-abl treated cells at 32° C. and 37° C.; FIGS. 9E and 9F show AS-bcr-abl treated cells at 32° C. and 37° C. Open circles=K562 parent; open squares=RP4 vector; and open triangles=DP160.

DETAILED DESCRIPTION OF THE PREFERRED EMBODIMENTS

Figure 1A:
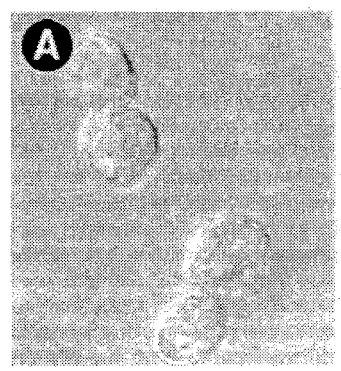
FIG. 1A–1D.
Figure 1B:
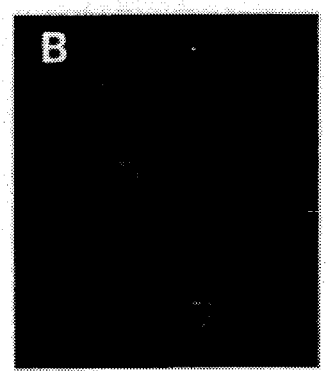

The present invention provides a method for enhancing the efficacy of therapeutic treatment of a cell to induce cell death, particularly in tumor cells which exhibit resistance to induction of apoptosis, by inhibiting the expression of an anti-apoptotic gene in the cell in conjunction with a therapeutic agent. Inhibition of gene expression is achieved by administering to the cell an antisense oligonucleotide sequence which is capable of hybridizing to the nucleic acid sequence of the anti-apoptotic gene. This antisense oligonucleotide inhibits, or down-regulates, the expression of the anti-apoptotic gene in a cell and, thus, enhances the susceptibility of the cell to induction of apoptosis. Down-regulation of an anti-apoptotic gene is useful, in conjunction with a therapeutic means for inducing cell death, for enhancing the efficacy of the treatment.

The target anti-apoptotic gene may already be known. For example, known anti-apoptotic genes include bcr-abl and bcl2. Alternatively, the particular gene may be unknown.

The present invention also provides a method for identifying an anti-apoptotic gene in a cell which is resistant to induction of apoptosis. In addition, the invention provides a method for identifying an agent which induces apoptosis in a cell.

The invention provides antisense oligonucleotides which reduce expression of an anti-apoptotic gene. An oligonucleotide according to the present invention has a sequence that is complementary to, and thus hybridizes with, the nucleic acid sequence of the target anti-apoptotic gene. However, absolute complementarity is not required. The nucleic acid sequence of the target gene can be either a DNA or an RNA sequence. The "nucleic acid sequence" of the target gene includes sequences upstream from the 5'-terminus of the structural gene, such as regulatory sequences, and sequences downstream from the 3'-terminus of the structural gene. Typically, the 5' and 3' sequences are about 100 nucleotides or less. An oligonucleotide is "complementary" to the nucleic acid sequence of the target gene, and thus useful according to the invention, if it is capable of forming a stable duplex with at least part of the RNA sequence of the gene so that processing or translation of the RNA is inhibited, or capable of forming a complex, such as a triplex, with genomic DNA of the gene so that promotion of transcription is inhibited or premature transcript termination is produced (Greene, et al., *Clinical Biotechnology*, 2:75, 1990). When the oligonucleotide hybridizes to the RNA of the target gene, stable duplex formation depends on the sequence and length of the hybridizing oligonucleotide and the degree of complementarity between the antisense oligonucleotide and the target sequence. The system can tolerate less fidelity (complementarity) when a longer oligonucleotide is used. However, oligonucleotides of about 8 to 40 bases in length and having sufficient complementarity to form a duplex having a melting temperature of greater than about 40° C. under physiologic conditions are particularly well suited for practice of the invention (Thoung, et al., *PNAS USA*, 84:5129, 1987; Wilson, et al., *Nucleic Acids Res.*, 16:5137, 1988; Maniatis, et al., *Molecular Cloning: A Laboratory Manual*, Cold Spring Harbor Laboratory Press, Cold Spring Harbor, N.Y., 1982). Accordingly, such oligonucleotides are preferred.

Another variable that may affect practice of the invention is the region of the target anti-apoptotic gene to which the selected oligonucleotide is designed to hybridize. The oligonucleotide can inhibit gene expression by hybridizing either to the RNA transcript or, less commonly, to the gene itself. Although oligonucleotides capable of stably hybridizing with any region of the nucleic acid sequence of the gene may be suitable for practice of the invention, oligonucleotides complementary to a region including the translation start site sequence of the anti-apoptotic gene are particularly effective. In a preferred embodiment, an oligonucleotide complementary to the bcr translation start nucleic acid sequence of the bcr-abl gene is utilized. Oligonucleotides complementary to an abl nucleic acid sequence of the bcr-abl gene can also be used according to the invention. However, the antisense nucleotide sequences of the invention do not require the presence of an antisense sequence to the breakpoint junction of the bcr-abl fusion gene. The antisense oligonucleotide is considered effective as long as the transcription or translation of the nucleic acid sequence to which the oligonucleotide is complementary, and thus the expression of the anti-apoptotic gene, is inhibited.

The invention includes antisense oligonucleotides which hybridize with the nucleotide sequences comprising 5'-ATG-GTGGACCCGGTGGGC-3' (SEQ ID NO: 1), or 5'-GC-CCTTCAGCGGCCAGTA-3' (SEQ ID NO: 2), corresponding to the translation start site of the bcr or abl regions of bcr-abl, respectively. In a preferred embodiment, when the antisense oligonucleotide sequence is complementary to the sense nucleic acid sequence of the translation start site of the bcr region of the bcr-abl gene, the preferred antisense comprises the sequence, 5'-GCCCACCGGGTCCACCAT-3' (SEQ ID NO: 3), and sequences complementary thereto. When the antisense oligonucleotide sequence is complementary to the sense nucleic acid sequence of the translation start site of the abl region of the bcr-abl gene, the preferred antisense comprises the sequence, 5'-TACTGGCCGCT-GAAGGGC-3' (SEQ ID NO: 4), and sequences complementary thereto.

The oligonucleotides employed may be unmodified or modified RNA or DNA molecules. Suitable modifications include, but are not limited to, the ethyl or methyl phosphorate modifications disclosed in U.S. Pat. No. 4,469,863, the disclosure of which is incorporated by reference, and the phosphorothioate modifications to deoxynucleotides described by LaPlanche, et al. (*Nucleic Acids Research*, 14:9081, 1986), and by Stec, et al., (*J. Am. Chem. Soc.*, 106:6077, 1984). The modification to the antisense oligonucleotide is preferably a terminal modification in the 5' or 3' region. Preferred are modifications of the 3' terminal region. Also preferred are modifications with methyl groups added to 5' carbon atoms as described by Saha, et al. (*CEN*, 44:44, 1993).

Furthermore, recent advances in the production of oligoribonucleotide analogues mean that other agents may also be used for the purposes described here, such as, 2'-methylribonucleotides (Inoue, et al., *Nucleic Acids Res.*, 15:6131, 1987) and chimeric oligonucleotides that are composite RNA-DNA analogues (Inoue, et al., *FEBS Lett.*, 215:327, 1987). Finally, DNA analogues, such as peptide nucleic acids (PNA) are also included (Egholm, et al., *Nature*, 365:566, 1993) and can be used according to the invention.

In order for the target cell to be rendered susceptible to apoptosis by the antisense oligonucleotide in accordance with the method of the invention, the cells must be exposed to the oligonucleotide under conditions that facilitate their uptake by the cells. In vitro therapy may be accomplished by a number of procedures, including, for example, simple incubation of the cells with the oligonucleotide in a suitable nutrient medium for a period of time suitable to enhance apoptosis. For example, where the cell targets of the antisense oligonucleotide of the invention are present in bone marrow cells, procedures can be employed such as those described by Gartner and Kaplan, *Proc. Natl. Acad. Sci. USA*, 77:4756, 1980; Coulombel, et al., *Blood*, 67:842, 1986, Meagher, et al, *Blood*, 72:273, 1988; or U.S. Pat. No. 4,721,096, with an optimal concentration of the selected antisense oligonucleotide. After the bone marrow cells have been exposed to the oligonucleotide and, in some cases, cultured as described above, the cells are then infused into the transplant recipient to restore hematopoiesis.

Antisense oligonucleotides according to the invention may be administered ex vivo by harvesting hematopoietic cells as well as other cell types, from a patient, treating them with the antisense oligonucleotide, then returning the treated cells to the patient before or after administration of an apoptotic methodology. Ex vivo techniques have been utilized in treatment of cancer patients and are well-known to those skilled in the art. For example, antisense oligonucleotides of the invention may be administered to bone marrow cells in conjunction with a therapeutic reagent for the purpose of bone marrow purging to enable in vitro elimination of CML cells having a bcr-abl gene. Administration can be carried out ex vivo by incubating a therapeutic reagent and an antisense oligonucleotide in a suitable carrier with the bone marrow harvested from the donor. Unincorporated antisense oligomers are removed from the cells by methods known in the art, and the bone marrow cells purged of the cells having the bcr-abl gene are then infused back into the patient.

In addition, antisense oligonucleotides according to the invention may also be administered in vivo. Antisense oligonucleotides can be administered as the compound or as a pharmaceutically acceptable salt of the compound, alone or in combination with pharmaceutically acceptable carriers, diluents, simple buffers, and vehicles. For example, expression vectors that produce antisense RNA can be engineered from DNA duplexes in the laboratory and introduced into cells (Weintraub, et al., *Sci. Amer.* 1:40, 1990). Most preferably, antisense oligonucleotides are mixed individually or in combination with pharmaceutically acceptable carriers to form compositions which allow for easy dosage preparation.

The antisense oligonucleotide of the invention can be administered to provide in vivo therapy to a patient having a disorder which is associated with bcr-abl. Such therapy can be accomplished by administering, ex vivo and in vivo as the case may be, a therapeutically effective amount of antisense oligonucleotide. The term "therapeutically effective" means that the amount of antisense oligonucleotide administered is of sufficient quantity to suppress, to some beneficial degree, expression of bcr-abl.

Antisense oligonucleotides according to the present invention can be administered to the patient in any acceptable manner including orally, by injection, using an implant, nasally and the like. Oral administration includes administering the oligonucleotides of the present invention in tablets, suspensions, implants, solutions, emulsions, capsules, powders, syrups, water compositions, and the like. Nasal administration includes administering the composition of the present invention in sprays, solution, and the like. Injections and implants are preferred because they permit precise control of the timing and dosage levels used for administration, with injections being most preferred. Antisense oligonucleotides are preferably administered parenterally.

Antisense oligonucleotide compositions can be administered in an injectable formulation containing antisense oligonucleotide-compatible and biocompatible carriers such as various vehicles, adjuvants, additives, and diluents to achieve a composition usable as a dosage form. Aqueous vehicles such as water having no nonvolatile pyrogens, sterile water, and bacteriostatic water are also suitable to form injectable antisense oligonucleotide formulations. In addition to these forms of water, several other aqueous vehicles can be used. These include isotonic injection compositions that can be sterilized such as phosphate buffered saline, sodium chloride, Ringer's, dextrose, dextrose and sodium chloride, gelatin and lactated Ringer's. Addition of water-miscible solvents, such as methanol, ethanol, or propylene glycol generally increases the solubility and stability of the compounds in these vehicles. Additionally various additives which enhance the stability, sterility, and isotonicity of the composition including antimicrobial preservatives, antioxidants, chelating agents, gelatin and buffers can be added. Any vehicle, diluent or additive used would, however, have to be compatible with the antisense oligonucleotides of the present invention.

In addition to administration with conventional carriers, the antisense oligonucleotides may be administered by a variety of specialized oligonucleotide delivery techniques. For example, oligonucleotides may be encapsulated in liposomes for therapeutic delivery. Oligonucleotides have been successfully encapsulated in unilameller liposomes and the delivery technique is well-known in the art. In addition, such vehicles as reconstructed Sendai virus envelopes may also be used to deliver the oligonucleotide (Arad, et. al., *Biochem. Biophy. Acta.*, 859:88, 1986). Further, antisense oligonucleotides may also be delivered in the form of poly(L- lysine) conjugates as described by Lemaitre, et.a/., (*Proc. Natl. Acad. Sci. USA*, 84:648, 1987).

Antisense oligonucleotide compositions according to the present invention can also be administered in the form of a slow-release subcutaneous implant which is inserted beneath the skin. The implant can take the form of a pellet which slowly dissolves after being implanted or a biocompatible, antisense oligonucle-otide-compatible delivery module well known to those skilled in the art. Such well known dosage forms are designed such that the active ingredients are slowly released over a period of several days to several weeks.

The antisense oligonucleotides of the invention are administered in an amount sufficient to inhibit the expression of the targeted anti-apoptotic gene. A "sufficient" amount, for purposes of the invention, is that amount of antisense oligonucleotide which achieves an observable increase in the susceptibility of the target cells to apoptosis as indicated by a measurable decrease in expression of the target gene. The invention also provides a method of monitoring the effectiveness of suppressing bcr-abl in the tissue of an individual after administering a therapeutically effective amount of bcr-abl antisense comprising detecting the level of bcr-abl expression in a tissue, before and after antisense therapy. Levels of bcr-abl can be detected by immunological methods such as ELISA, or nucleic acid methods, such as Northern blot analysis of bcr-abl mRNA.

For ex vivo application, such as bone marrow purging, the antisense oligonucleotides to bcr-abl are administered to cells in an amount sufficient to increase the susceptibility of the cells to apoptosis, such that a therapeutic treatment for inducing tumor cell death effectively kills a cell having bcr-abl while maintaining the viability of normal hematologic cells. Such amounts may vary depending on the condition of the patient, the sensitivity of the tissue to antisense and the therapeutical treatment, as well as other factors. Those of skill in the art can readily evaluate these factors and, thus, determine the particular therapeutically effective concentration of antisense oligonucleotide without undue experimentation. Preferably, the method is used on a patient with CML.

For in vivo use, antisense oligonucleotide according to the invention can be administered in a single dose or can be administered in multiple doses over a period of time, generally by injection. Various administration patterns will be apparent to those skilled in the art. The dosage ranges for the administration of the antisense oligonucleotide of the invention are those large enough to produce the desired effect of down-regulating the expression of the target anti-apoptotic gene, and thus of rendering the target cells more susceptible to apoptosis. The dosage should not be so large as to cause adverse side effects. Generally, the dosage will vary with the age, condition, sex and extent of the disease in the patient and can be determined by one of skill in the art without undue experimentation. The dosage can be adjusted by the individual physician in the event of any counter indications, immune tolerance, or similar conditions. Those of skill in the art can readily evaluate such factors and, based on this information, determine the particular therapeutically effective concentration of antisense oligonucleotide. Generally, dosages for the antisense oligonucleotide can vary from about 1.0 mg/g body weight to about 100 mg/g body weight, preferably from about 10 mg/g body weight to about 80 mg/g body weight, most preferably from about 30 mg/g to about 50 mg/g body weight.

In a therapeutic treatment method according to the invention, before, during or after administration of antisense oligonucleotide, at least one therapeutic agent or method capable of inducing apoptosis in a cell is used to induce cell death. For example, chemical agents that are often used in chemotherapy can be used to induce apoptosis. Such agents include but are not limited to cisplatin (Barry, et al., *Blochem. PharmacoL* 40:2353, 1990), etoposide (Kaufman, *Cancer Res.*, 49:5870, 1989), teniposide (Del Bino, et al., *Cancer Res.*, 51:1165, 1991; Bertrand, et al., *Cancer Res.* 51:6280, 1991), DNA alkylating agents (O'Connor, et al., *Cancer Res.* 51:6550, 1991), actinomycin D, macromolecular synthesis inhibitors (Martin, et al., *J. Immunol*, 145:1859, 1990) and others. Physical treatments capable of inducing apoptosis can also be used. Such physical treatments include, for example γ-radiation (Kruman, et al., *J. Cell. Physiol.*, 148:267, 1991), ultraviolet light (Martin, et al., *Int. J. Rad. Biol.*, 59:1001, 1991), heat shock (Barry, et al., *Biochem. Pharmacol.*, 40:2353, 1990), and cold shock (Soloff, et al. *Biochem. Biophys. Res. Commun.* 145:876, 1987). All of these therapeutic treatments are well known in the art and are herein incorporated by reference.

Subsequent to, or simultaneous with, the administration of the antisense oligonucleotide, the target cells are exposed to a condition which is capable of inducing apoptosis in cells susceptible to induction of apoptosis. Such conditions include those previously mentioned. Mention is made in particular of actinomycin D, etoposide (VP-16), cyclohex-imide or topoisomerase inhibitors such as VM-26 (Liu, et al., *Ann. Rev. Biochem.* 58:351, 1989) and camptothecin. Other appropriate conditions, such as serum withdrawal or growth factor withdrawal, for example withdrawal of IL-3 in an IL-3 dependent cell line, can likewise be employed.

The present invention also provides a method for identifying previously unknown anti-apoptotic genes in cells resistant to the induction of apoptosis. In this embodiment, the target cells are administered an antisense oligonucleotide which is capable of hybridizing to a nucleic acid sequence of a gene expressed in the cell and suspected of being an anti-apoptotic gene. The antisense oligonucleotide is administered in an amount sufficient to inhibit the expression of the gene. The inhibition of the gene expression is determined by detecting the decrease in the level of mRNA for the gene, or the level of protein expression of the gene, using any suitable means known to the art, such as nucleic acid hybridization or antibody detection methods, respectively.

According to this embodiment, the cells are subsequently observed in order to determine whether apoptosis has been induced as a result of the foregoing treatment. Typically, the cells are observed for morphological changes, such as chromatin condensation, cell shrinkage, increased granularity and other indicia of apoptosis known to those of skill in the art. Chromatin condensation can be detected by standard methods, such as light microscopy of stained cell preparations. Cell shrinkage and granularity can be readily detected by measuring the light scattering properties of the cells (Kerr, et al. supra., and Wyllie, et al., supra).

Observation of single or double stranded fragmentation of DNA into oligonucleosomal ladders often is another indication that apoptosis has been induced (Arend, et al., *Am. J. Pathol*, 136:593, 1990; Wyllie, et al., *J. Pathol*, 142.:67, 1984). Sometimes, however, apoptotic cells do not exhibit double stranded internucleosomal DNA fragmentation (Collins, et al., *Int. J. Rad. Biol.*, 62:45 1992; Cohen, et al., *Biochem. J.*, 286:331 1992); instead, single DNA strand breaks will be observed. Single-strand breaks can readily be detected using a method of in situ nick end-labelling of the DNA. This method is described by Wyllie, et al. (*Br. J. Cancer,* 67:20, 1993).

The invention is illustrated by reference to the following example employing the CML K562 cell line. Other cells, including but not limited to CML granulocytes isolated from patients, can also be used. It will be appreciated that the invention can be practiced other than as exemplified.

The invention also provides a method for identifying an apoptotic agent comprising contacting a cell with an antisense oligonucleotide which is complementary to an anti-apoptotic nucleic acid sequence followed by, or simultaneously with contacting the cell with the putative apoptotic agent, and observing the effect on the cell for apoptosis. For example, an antisense oligonucleotide of the invention, such as one complementary to the sense nucleic acid sequence of the translation start site for bcr or abl of bcr-abl may be administered to a cell, followed by treatment of the cell with a potential apoptotic agent. The effectiveness of the agent in inducing apoptosis is measured by any of the above-mentioned indicia typical of apoptosis.

The invention also provides a pharmaceutical combination comprising an antisense oligonucleotide sequence which is complementary to the sense nucleic acid sequence of the translation initiation site of an anti-apoptotic nucleic acid in combination with a therapeutic agent. The term "pharmaceutical combination" as used herein includes mixtures of the two components and also non-mixed associations, such as those found in kits or pharmaceutical packages. The anti-apoptotic antisense oligonucleotide may include an oligonucleotide complementary to the sense nucleic acid sequence of the translation initiation site bcr or abl of bcr-abl. The therapeutic agent is typically one as described above, such as cisplatin, actinomycin D, or DNA alkylating agents.

The following examples are intended to illustrate but not limit the invention. While they are typical of those that might be used, other procedures known to those skilled in the art may alternatively be used.

EXAMPLE 1

Materials and Methods

1. Cell culture

K562 and HL60 cells were maintained in a 5% $CO_2$ atmosphere at 37° C. Exponentially growing cells were used unless otherwise stated.

2. Antisense treatment

Cells ($5\times10^5$ /ml) were incubated with either 10 μmol/L antisense or 10 μmol/L nonsense oligonucleotide, and subsequently treated with apoptosis inducing stimuli. Phosphorothioate-derivatized oligodeoxynucleotides (Regional DNA Synthesis, Calgary, Canada) to the first 18 translated bases of the bcr-abl mRNA or the abl nucleotide portion of the bcr-abl gene were used. A random sequence of the same bases was used as a nonsense control. Oligonucleotides were also synthesized by previously described methods (Zon, et al., *Anti-Cancer Drug Design* 6:539, 1991) After incubation, cells were fixed in 70% ice-cold ethanol for 30 minutes and permeablilized in a 2.5% paraformaldehyde solution containing 0.1% Triton X-100. Unreacted aidehyde groups were blocked by washing with a phosphate-buffered saline (PBS) solution containing 0.1 mol/L glycine before incubation with a sheep anti-abl antibody (Serotech, UK) for 30 minutes at room temperature. After a washing step a fluoroscein isothioate (FITC) labeled donkey anti-sheep antibody was added and fluorescence viewed with a laser scanning microscope.

3. Induction of apoptosis

Cells were seeded at $5\times10^5$ /ml in medium and exposed to the apoptosis inducing stimuli at the stated concentrations. Stock solutions of actinomycin D, camptothecin, etoposide (VP-16), and cyclohexamide (all from Sigma, Poole, Dorset, UK) were made up using dimethyl sulfoxide (DMSO) as a solvent. For experimental work such as solutions were diluted at least 1:500 before use to ensure a DMSO concentration of less than 0.2%. Appropriate controls were run in all cases. Incubation times were as outlined below and all incubations were performed at 37° C. In addition, serum deprivation was also used as an additional stimulus to induce apoptosis.

4. Assessment of cell viability and apoptosis

Cell viability was assessed by their ability to exclude trypan blue. Cell morphology was evaluated on Leukostat (Fisher Scientific, Orangeburg, N.Y.) stained cytocentrifuge cell preparations. Apoptotic cells were identified morphologically using previously defined criteria (Wyllie, et al., *Int. Rev. Cytol.* 68:251, 1980; Martin, et al., *Clin. Exp. Immunol.* 79: 448, 1990). These included cytoplasmic condensation and compaction of chromatin. In addition two other methods were used to measure the levels of apoptosis in K562 cells. These included the use of flow cytometry to quantify the level of forward light scatter in cells undergoing apoptosis. A decrease in forward light scatter has been previously shown to be indicative of apoptosis (Cotter, et al., *Cancer Res.* 52:997, 1992). Finally, an in situ terminal deoxynucleotidyl transferase assay (TDTA) was used to measure nick end-labeling of DNA because K562 and other cells have been shown not to undergo internucleosomal DNA cleavage as they die via apoptosis.

5. Western immunoblotting

Protein extracts from K562 cells were electrophoresed in polyacrylamide gels, transferred to a nitrocellulose membrane, and probed for expression of bcr-abl as described (Shi, et al., *Science* 257:212, 1992). Because abl occurs as a fusion protein with bcr in K562 cells, a sheep anti-abl antibody (Serotech, UK) was used to detect levels of the 210 kD bcr-abl protein.

EXAMPLE 2

Effect of Oligonucleotide on Anti-Apoptotic Gene Expresssion

1. Induction of Apoptosis in Cell Lines

Five lines of human hematopoietic cells were subjected to four distinct regimens for the induction of apoptosis. The regimens were as follows: (a) exposure to actinomycin D (5 μg/ml) for 4 hrs at 37° C.; (b) exposure to etoposide (25 μg/ml) for 4 hrs at 37° C.; (c) exposure to UV radiation (302 nm) for 5 min followed by incubation for 4 hrs; and culture in the absence of fetal bovine serum for 48 hrs. The cells were then examined for morphological evidence of apoptosis by methods described by Collins, et al., *Science*, 225:72, 1984; Kerr, et al., *Brit. J. Cancer*, 26:239, 1972; and Wyllie, et al., *Int. Rev. Cytol.*, 68;251, 1980. Cell lines used were: promyelocytic leukemia line HL-60 (ATCC CCL 240); monocytic line U937 (ATCC CRL 1593); T-lymphocyte line Molt-4 (ATCC CRL 1582); B-lymphocyte line Daudi (ATCC CCL 213); and erythroid (CML) line K562 (ATCC CCL 243). Results are set forth in Table 1:

TABLE 1

| Treatment | Cell line | % Apoptotic Cells |
| --- | --- | --- |
| Actinomycin D | HL-60 | 48 +/– 3.2 |
| | U937 | 20 +/– 2.7 |
| | Molt 4 | 15 +/– 1.1 |
| | Daudi | 10 +/– 1.6 |
| | K562 | 4 +/– 0.2 |
| Etoposide | HL-60 | 30 +/– 2.2 |
| | U937 | 15 +/– 0.9 |
| | Molt 4 | 10 +/– 0.8 |
| | Daudi | 7 +/– 0.5 |
| | K562 | 5 +/– 0.3 |
| UV Irradiation | HL-60 | 98 +/– 1.5 |
| | U937 | 96 +/– 2.0 |
| | Molt 4 | 48 +/– 4.3 |

TABLE 1-continued

| Treatment | Cell line | % Apoptotic Cells |
| --- | --- | --- |
| Serum Starvation | Daudi | 20 +/– 1.8 |
| | K562 | 8 +/– 0.5 |
| | HL-60 | 85 +/– 5.1 |
| | U937 | 82 +/– 3.6 |
| | Molt 4 | 41 +/– 3.2 |
| | Daudi | 39 +/– 2.8 |
| | K562 | 17 +/– 1.5 |

All results are the mean +/– SEM of triplicate determinations. As shown in Table 1, only CML cell line K562 displayed significantly more resistance to the induction of apoptosis than other human hematopoietic cell lines. This resistance did not appear to be related to the type of inducing agent used.

2. Effect of Oligonucleotide on Expression of bcr-abl Gene

Figure 1C:
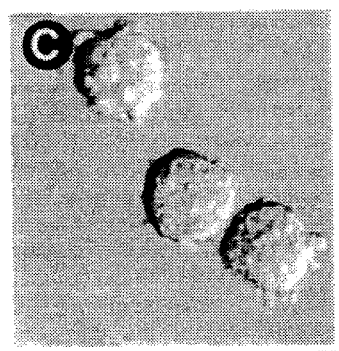
Figure 1D:
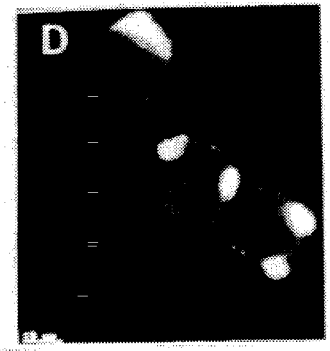

An antibody staining method was used to determine the level of expression of the bcr-abl gene in K562 cells. A sheep anti-Abl antibody (Serotech, UK) was used. Since Abl occurs as a fusion protein with Bcr in K562 cells, this antibody was used to detect levels of the Bcr-Abl fusion protein. K562 cells which had been treated with either anti-sense (AS) bcr-abl oligonucleotides, (more particularly oligodeoxynucleotide), or its non-sense (NS) counterparts for 48 hours were fixed and permeabilized in a 2.5% paraformaldehyde solution containing 0.1% Triton X-100 and incubated with sheep anti-abl antibody. Unreacted aidehyde groups were blocked by washing with a Tris glycine solution prior to incubation with the sheep anti-Abl antibody for 30 min at room temperature. Following a washing step an FITC labeled donkey anti-sheep antibody was added and fluorescence viewed with a laser scanning microscope. FIG. 1A shows Nomarski and B) fluorescent images of AS-bcr-abl treated cells; FIG. 1C shows Nomarski and D) fluorescent images of NS-bcr-abl treated cells.

A positive control was run to establish base line levels of c-abl expression, a level which was not affected if cells were treated with the non-sense oligonucleotides. Cells exposed to the anti-sense oligonucleotides showed a decreased expression of the bcr-abl protein.

Figure 2:
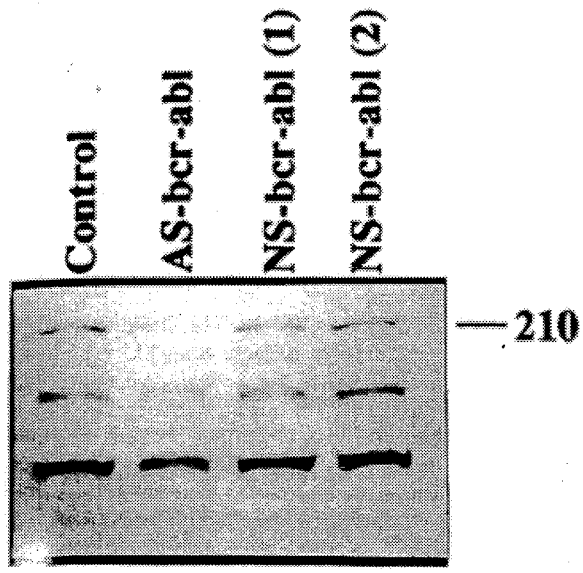
FIG. 2 is a Western blot performed on protein extracts of K562 cells treated with either AS-bcr-abl 5'-GCCCAC-CGGGTCCACCAT-3' (SEQ ID NO: 3) or two distinct NS-bcr-abl: 5'-CGCGCCTCGTCCCAAGCA-3' (SEQ ID NO: 5) and 5'-CGCCCTCGTTCCCAAGCA-3' (SEQ ID NO: 6).

In addition, a Western blot was performed on protein extracts of K562 cells treated with either AS-bcr-abl 5'-GCCCACCGGGTCCACCAT-3' (SEQ ID NO:3) or two distinct NS-bcr-abh 5'-CGCGCCTCGTCCCAAGCA-3' (SEQ ID NO: 5) and 5'-CGCCCTCGTTCCCAAGCA-3' (SEQ ID NO: 6). (see for example, Coligan, et al., Current Protocols in Immunology, Wiley Interscience, 1991). The Western blot supported the observation with the antisense oligonucleotide above. Expression of the 210-kD bcr-abl protein was decreased after treatment with antisense-bcr-abl, but two different nonsense bcr-abl oligonucleotides had no effect (FIG. 2).

3. Effect of bcr-abl Antisense Oligonucleotides on Induction of Apoptosis in K562 Cells K562 cells were cultured in RPMI 1640 medium supplemented with 10% fetal bovine serum. Phosphorothioate-derivatized oligonucleotides (10 µM) (Regional DNA Synthesis, Calgary, Canada) were added and cells incubated for 48 hrs to reduce intracellular levels of the bcr-abl protein. Following this pretreatment cells were exposed to apoptosis inducing conditions for 24 hours or 48 hours. Then apoptosis was quantified by morphological examination as described previously. The oligonucleotide sequences were as follows: antisense bcr-abl 5'-GCCCACCGGGTCCACCAT-3' (SEQ ID NO: 3); nonsense bcr-abl 5'-CGCGCCTCGTCCCAAGCA-3' (SEQ ID NO: 5). The conditions for the induction of apoptosis were as follows: 5 µg/ml actinomycin D, 5 µg/ml camptothecin, 5 µg/ml VP-16, 25 µg/ml cycloheximide or depletion of serum at 37° C.

Figure 3:
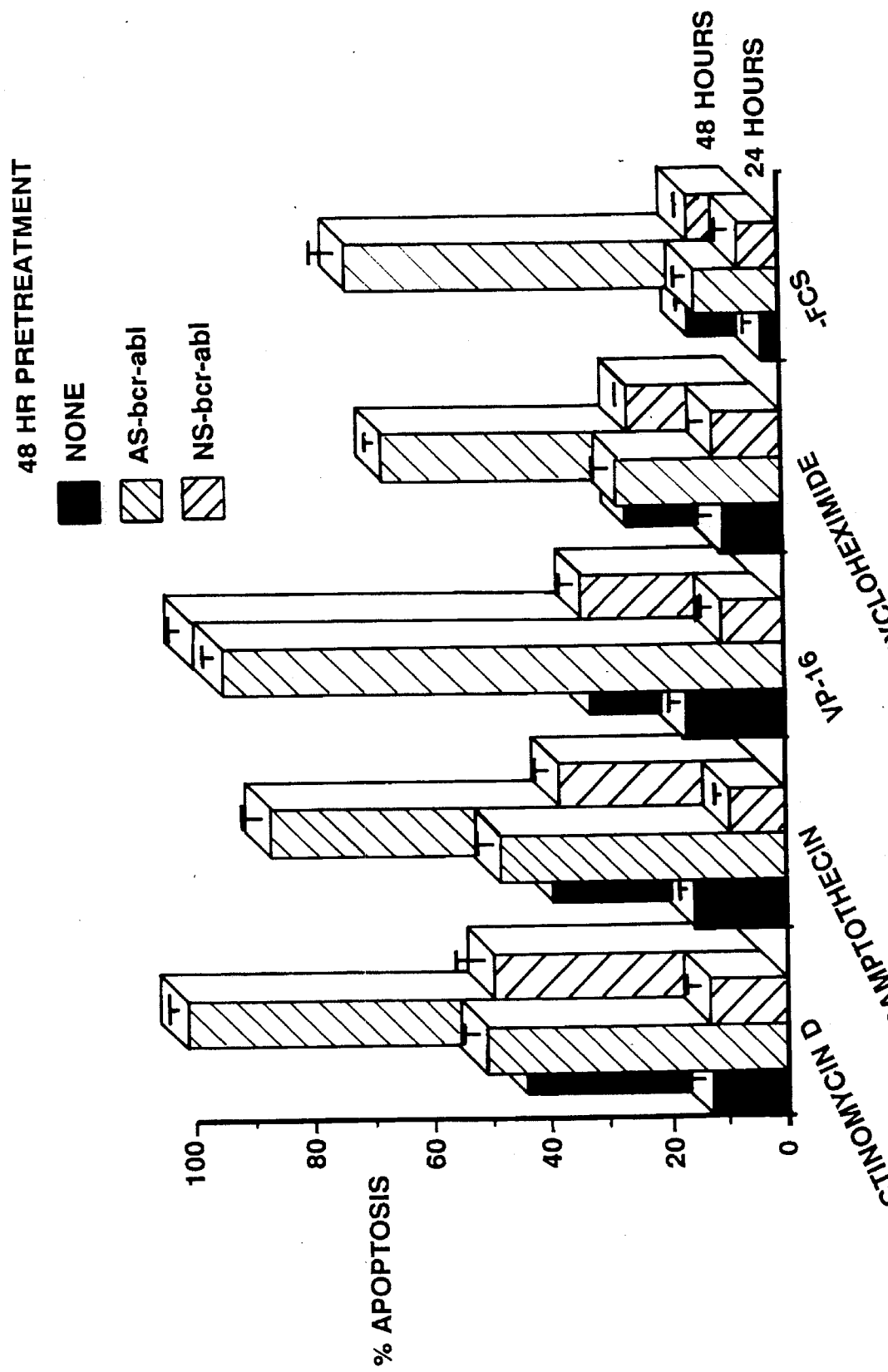
FIG. 3 is a diagram showing percent apoptosis in K562 cells treated with the anti-sense or nonsense oligonucleotide and exposed to actinomycin D, camptothecin, etoposide (VP-16), cycloheximide, or withdrawl of serum (-FCS).

As shown in FIG. 3, cells treated with the anti-sense oligonucleotide and exposed to actinomycin D, camptothecin, etoposide (VP-16), cyclohexamide, or withdrawl of serum were more susceptible to the induction of apoptosis than untreated cells or cells treated with the nonsense oligonucleotide.

Figure 4A:
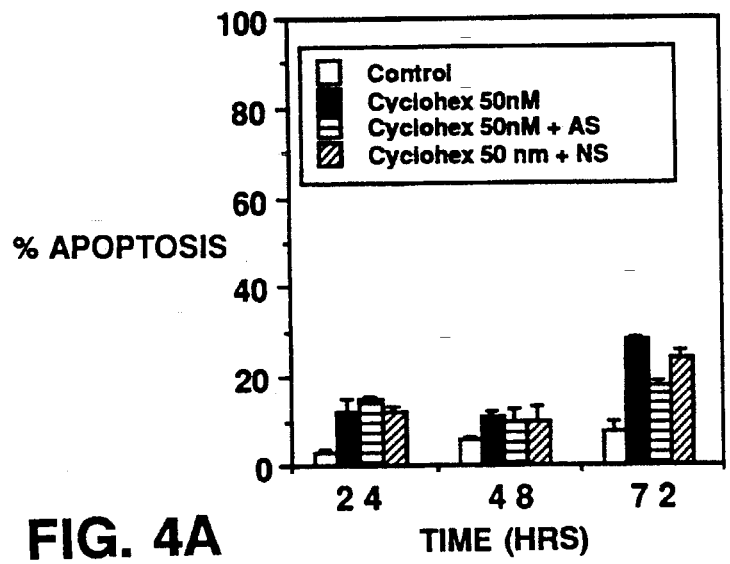
FIG. 4 is a diagram which shows HL-60 cells pretreated with either 10 μM AS-bcr-abl, 10 μM NS-bcr-abl, 10 μM VP-16, 50 nm cycloheximide, or 1 μM VM-26 for 24, 48, or 72 hours. The level of apoptosis in cell cultures was measured by morphologic means.
Figure 4B:
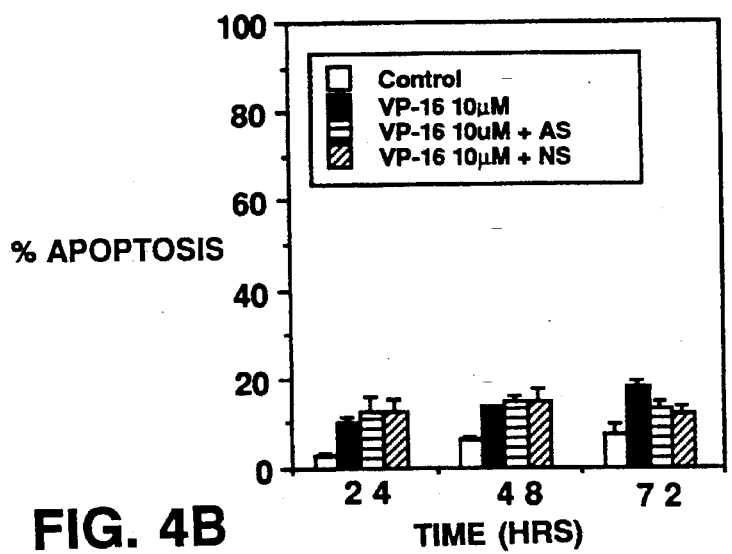
Figure 4C:
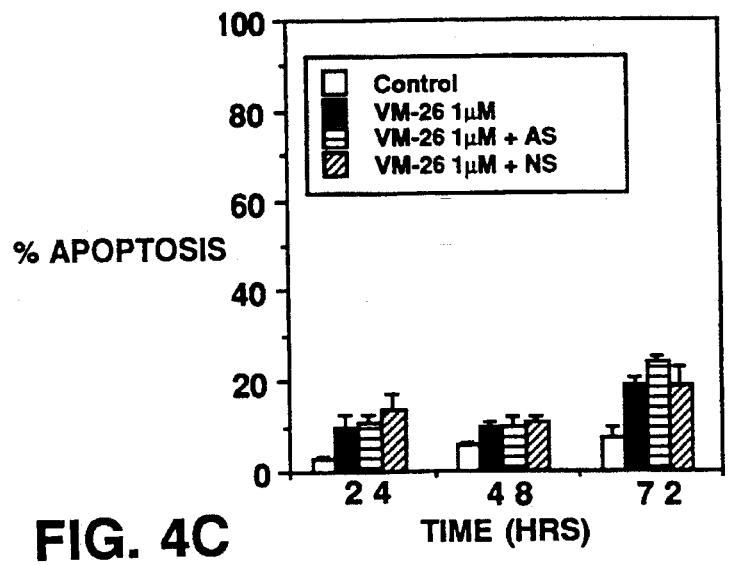

As a control for the effectiveness and specificity of the bcr-abl antisense, HL-60 cells, which do not express bcr-abl, were treated with the antisense oligonucleotides similarly to the K562 cells. HL-60 cells were pretreated with either 10 µM AS-bcr-abl, 10 µM NS-bcr-abl, 10 µM VP-16, 50 nm cyclohexamide, or 1 µM VM-26 for 24, 48, or 72 hours and the level of apoptosis in cell cultures was measured by morphologic means. FIG. 4 shows that AS-bcr-abl did not enhance apoptosis in the non-bcr-abl expressing HL-60 cell line treated with cyclohexamide, VP-16 or VM-26. These results show that the effect seen for K562 cells is probably mediated through downregulation of the bcr-abl gene rather than a non-specific effect of the oligonucleotides.

Figure 5A:
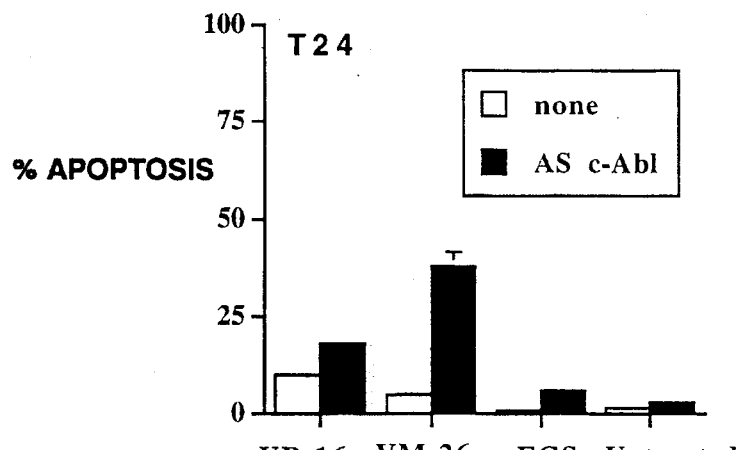
FIG. 5 is a diagram showing the induction of apoptosis in K562 cells incubated with antisense (AS) c-abl following treatment with etoposide (VP-16), VM-26, or serum depletion (-FCS).
Figure 5B:
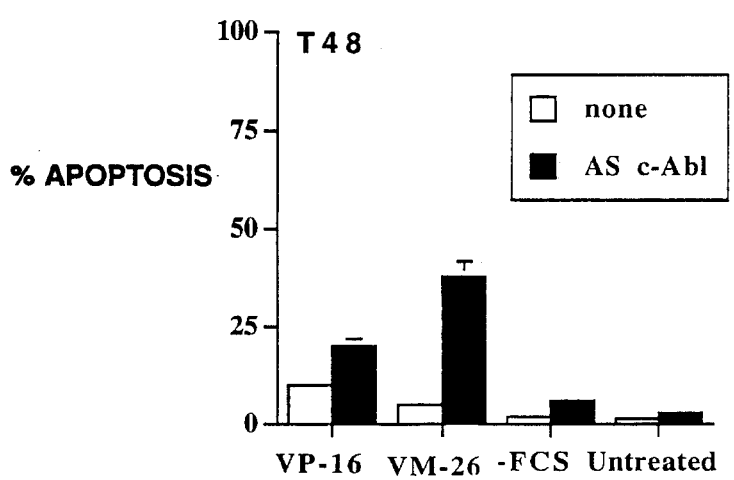
Figure 5C:
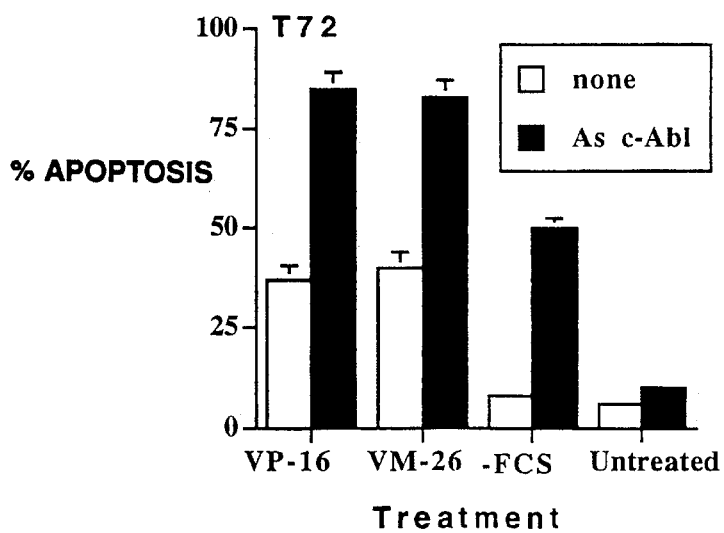

The effect of antisense against abl nucleotide portion of the bcr-abl gene was also examined. K562 cells were cultured in RPMI 1640 medium supplemented with 10% fetal bovine serum. Phosphorothioate-derivatized oligonucleotides (10 µM) (Regional DNA Synthesis, Calgary, Canada) were added and cells incubated in the presence of apoptosis inducing agents for 24, 48 and 72 hrs to reduce intracellular levels of the bcr-abl protein. The oligonucleotide sequence was as follows: antisense abl 5'-TACTGGCCGCTGAAGGGC-3' (SEQ ID NO: 4). The conditions for the induction of apoptosis were as follows: 25 µg/ml VP-16, 25 µg/ml VM-26, and depletion of serum (-FCS) at 37° C. The apoptosis was quantified by morphological examination as described herein. As shown in FIG. 5, cells treated with anti-sense oligonucleotide were more susceptible to the induction of apoptosis than untreated cells.

Figure 6A:
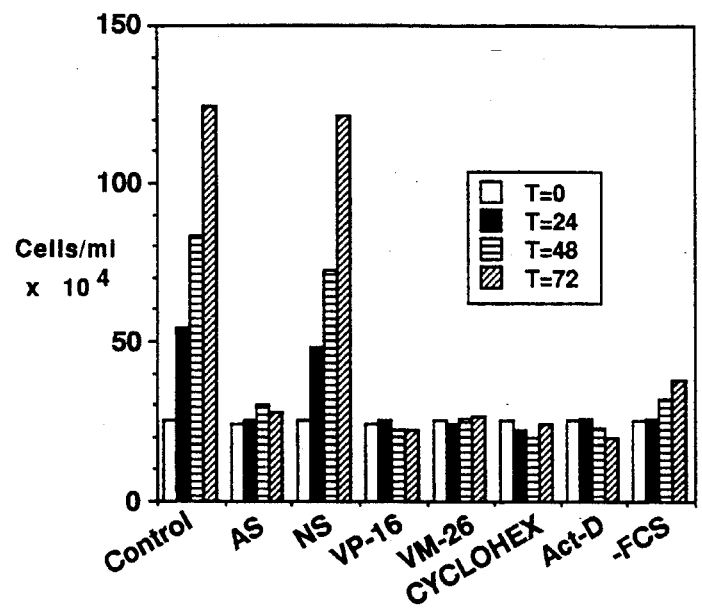
FIG. 6A shows the effect on proliferation after treatment of K562 cells with antisense (AS)-bcr-abl, nonsense (NS) bcr-abl, VP-16, VM-26, cycloheximide, actinomycin D and serum depletion (-FCS) at 0, 24, 48, and 72 hours after treatment.
Figure 6B:
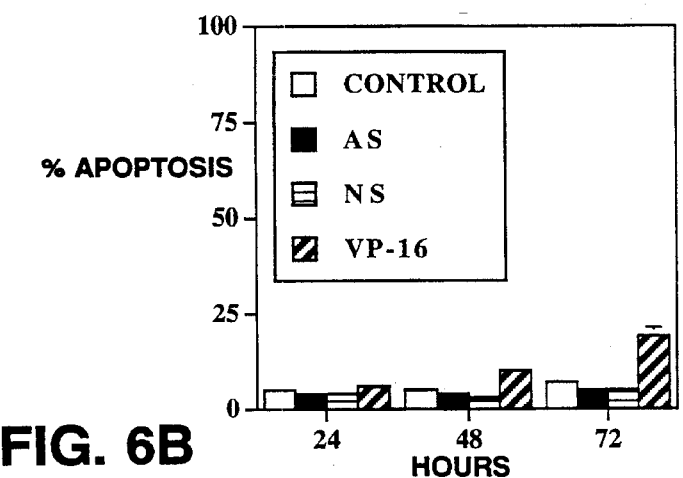
FIG. 6B shows the percent apoptosis at 24, 48, and 72 hours after treatment of K562 cells with VP-16, VM-26, cycloheximide, actinomycin D, serum depletion (-FCS), antisense (AS)-bcr-abl, or nonsense (NS) bcr-abl.
Figure 6C:
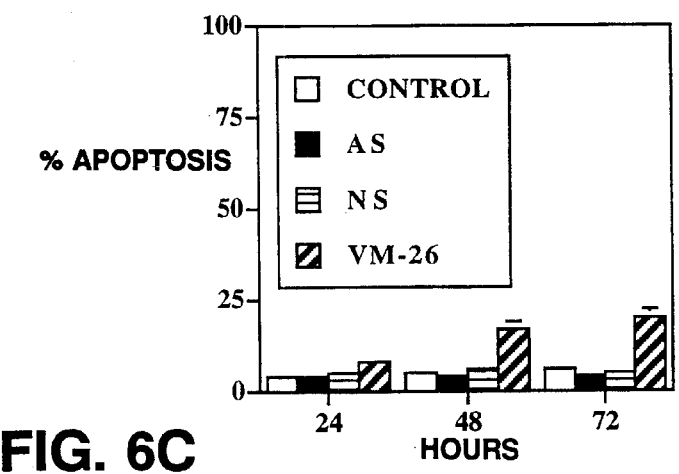

The percent apoptosis is a function of both cell death and proliferation. Therefore it was necessary to determine whether AS-bcr-abl inhibited cell proliferation, leading to a perceived increase in the level of apoptosis without having a direct effect on the process itself. To investigate this possibility, cells were treated with a number of agents including AS-bcr-abl that are known to inhibit cell proliferation. FIG. 6A shows the effect on proliferation after treatment of K562 cells with antisense (AS)-bcr-abl, nonsense (NS) bcr-abl, VP16, VM-26, cyclohexamide, actinomycin D and serum depletion at 0, 24, 48, and 72 hours after treatment. FIG. 6B shows the percent apoptosis at 24, 48, and 72 hours after treatment of K562 cells with VP-16 , VM-26, cyclohexamide, actinomycin D, serum depletion (-FCS), antisense (AS)-bcr-abl or nonsense (NS) bcr-abl.

FIG. 6A shows that AS, VP-16 , VM-26, cyclohexamide, actinomycin D and serum depletion all inhibited cell proliferation. NS-bcr-abl had no detectable effect on proliferation. FIG. 6B demonstrates that none of these agents alone had any effect on apoptosis. Taken together, the data indicate that AS-bcr-abl directly affects the process of apoptosis, rather than ind inhibition of proliferation.

EXAMPLE 3

Cell Shrinkage and DNA Fragmentaions Studies As Indicators of Apoptosis

Additional criteria which show that the form of cell death is apoptotic in nature includes cell shrinkage, which can be measured by light scattering properties. Cell shrinkage due to antisense treatment was detected by measuring the light scattering properties of treated cells using a FACScan flow cytometer. K562 cells (2×10⁶ /ml) were incubated with either 10 μM antisense or 10 μM nonsense and deprived of serum for a period of 72 hrs. Cells were fixed in 70% ice cold ethanol for 30 min. on ice prior to analysis on a Becton Dickinson FACScan. Results in FIG. 7 show ungated data for forward light scatter (x-axis) versus side light scatter (y-axis). This type of flow cytometry pattern is characteristic of apoptosis. The K562 cells did not display changes in light scattering properties upon treatment with AS-bcr-abl or serum withdrawl alone, however, the combination induced apoptosis as evidenced by the sharp decrease in forward light scatter.

Another characteristic feature of apoptosis is single-stranded DNA fragmentation (Gaviell, et al. *J. Ceil. Biol.* 119:493, 1992; Cohen, et al., *Cancer Res.* 52:997, 1992). A nick end-labeling assay was used to detect the single DNA strand breaks associated with apoptosis after antisense treatment. Single-stranded breaks were readily shown using this in situ DNA labeling method. Cells treated with AS-bcr-abl or NS-bcr-abl were deprived of serum for 48 hours and examined. K562 cells (5×10⁵ /ml) were fixed in 1% formaldehyde in PBS (pH 7.4) for 15 mins on ice, then resuspended in ice-cold 70% ethanol and transferred to a freezer. The cells were stored in ethanol at −20° C. for up to 24 hrs before being subjected to the terminal deoxynucleotide transferase assay (TDTA). Following re-hydration in PBS, 10⁵ cells were resuspended in 50 μl of a solution containing 0.1 M sodium cacodylate (pH 7.0), 0.1 mM dithiothreitol, 0.05 mg/ml bovine albumin, 5 units of terminal deoxynucleotidyl transferase and 0.5 nM biotin-16-dUTP. The cells were incubated in this solution at 37° C. for 30 mins, then rinsed in PBS and resuspended in 100 μl of a staining buffer which contained saline-sodium citrate buffer, 0.1% Triton X-100 and 5% (w/v) non-fat dry milk. The cells were incubated in this buffer for 30 min at room temperature in the dark. Cell fluorescence was measured using the LYSYS II software on a FACScan Flow Cytometer (Becton Dickinson, San Jose, Calf. USA).

Figure 8:
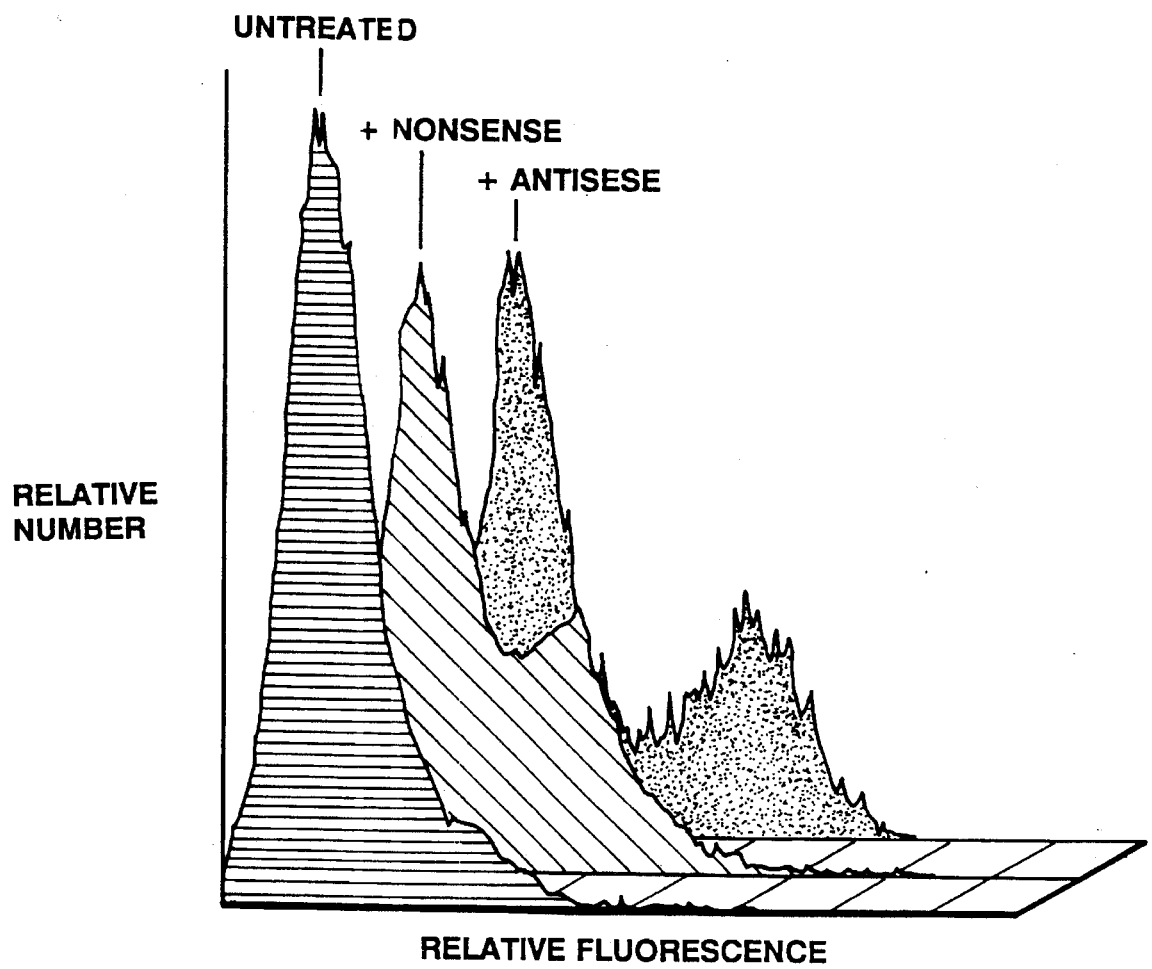
FIG. 8 is an early detection of DNA strand breaks occurring during apoptosis by using a FACScan Flow cytometer to measure incorporated biotinylated dUTP at sites of DNA breaks.

Results are shown in FIG. 8. The diagram shows untreated cells, as well as cells which had been treated with either nonsense or antisense and subsequently cultured in serum depleted medium to induce apoptosis. (X-axis=relative fluorescence; Y-axis=cell number.) The profile of the untreated cells was identical to that seen for the nonsense treated cells. The antisense treated cells showed a pronounced increase in single strand breaks, indicating that apoptosis had occurred.

EXAMPLE 4

Kinase Activity of abl is Essential to Apoptotic Resistance

To confirm that the ability of the antisense bcr-abl oligonucleotide to induce susceptibility to apoptosis corresponds to its ability to down-regulate bcr-abl levels in the cells, the effect of antisense to bcr-abl in K562 cells expressing another anti-apoptotic gene, namely v-abl, was examined. The v-abl gene differs in its translation start from bcr-abl and thus was expected to be unaffected by the antisense oligonucleotide targeted to the bcr-abl gene. The v-abl gene was also thought to inhibit apoptosis induced by growth factor withdraw-al. It was therefore expected that, if AS-bcr-abl mediates its effects only through the targeting and down-regulation of bcr-abl expression, which renders the cells susceptible to induction of apoptosis, then the presence of the v-Abl protein should reverse this effect.

Stable transfectants were generated (by electroporation) with constitutive expression of a temperature sensitive v-Abl (v-Abl$^{ts}$) (DP160) (J.Wang, University of California, San Diego) or with vector alone (pRP4) (derived from Invitrogen pREP4 by removal of EBNA-1 gene), and these together with parental K562 cells were tested for their susceptibility to etoposide-induced apoptosis following treatment with oligonucleotide. During the exposure to etoposide, cells were maintained at permissive (32° C.) or nonpermissive (37° C.) temperature for the v-Abl$^{ts}$. v-Abl$^{ts}$ is only expressed at the permissive temperature. Stable transformants were selected for hygromycin (500 μg/ml) resistance, subcloned, and subclones analyzed for v-ab/expression using reverse transcriptase-polymerase chain reaction.

FIG. 9 is a diagram showing the susceptibility of K562 cells expressing v-Abl to etoposide-induced apoptosis following treatment with oligonucleotides, nonsense-bcr-abl (NS) and antisense bcr-abl (AS). FIGS. 9A and 9B show control cells at 32° C. and 37° C.; 9C and 9D show NS-bcr-abl treated cells at 32° C. and 37° C.; FIGS. 9E and 9F show AS-bcr-abl treated cells at 32° C. and 37° C. Apoptosis was determined by morphologic assessment of haematoxylin-stained cytospin preparations of the cells.

Figure 9A:
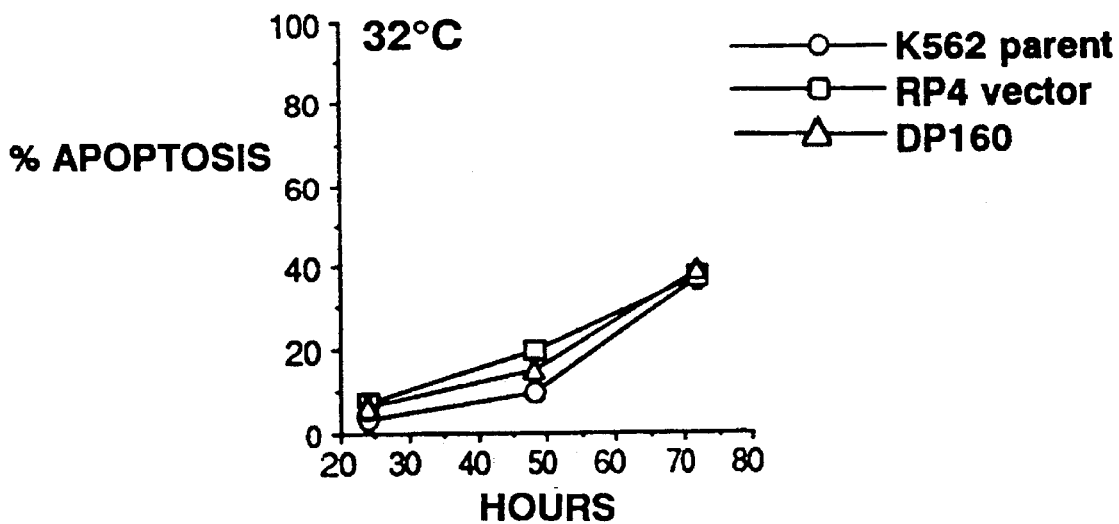
FIG. 9A–9F is a diagram showing the susceptibility of K562 cells expressing vAbl to etoposide-induced apoptosis following treatment with oligonucleotides, nonsense-bcr-abl (NS) and antisense bcr-abl (AS).
Figure 9B:
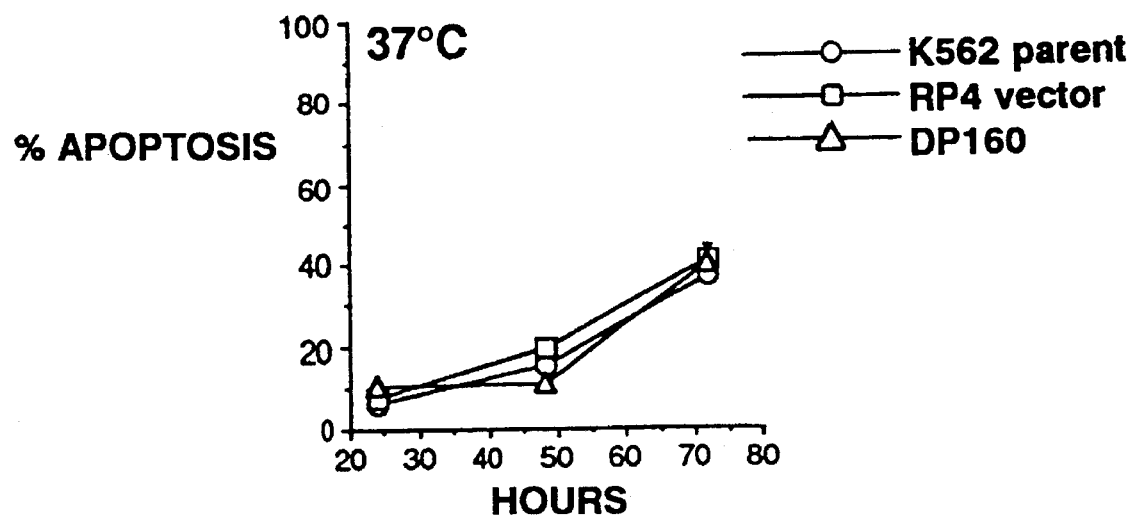
Figure 9C:
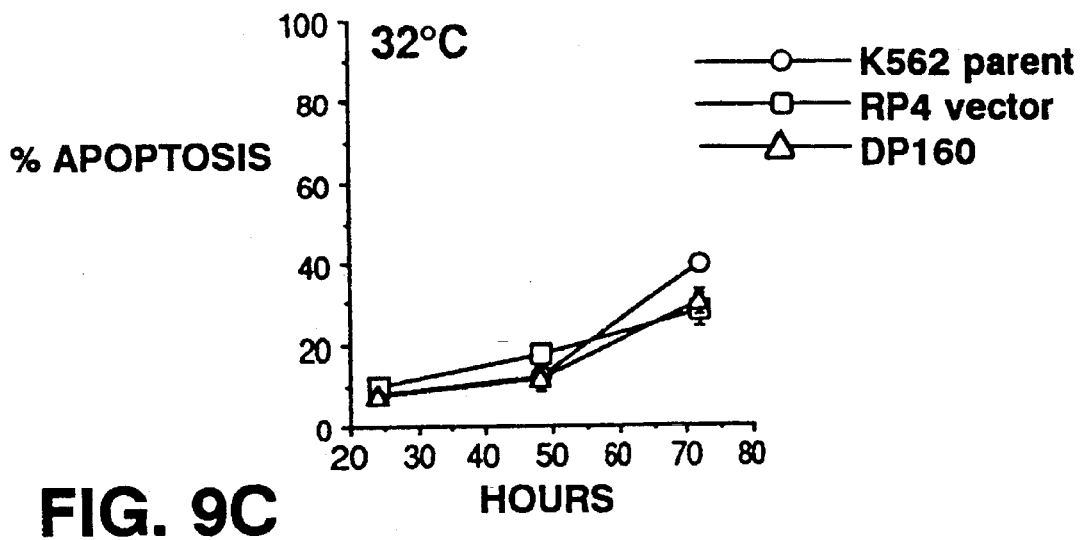
Figure 9D:
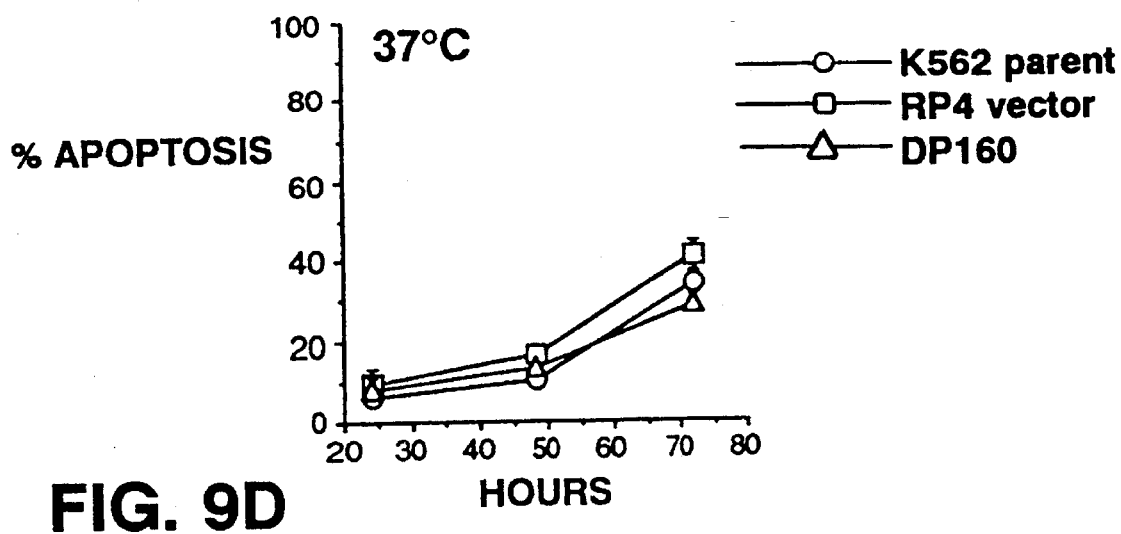
Figure 9E:
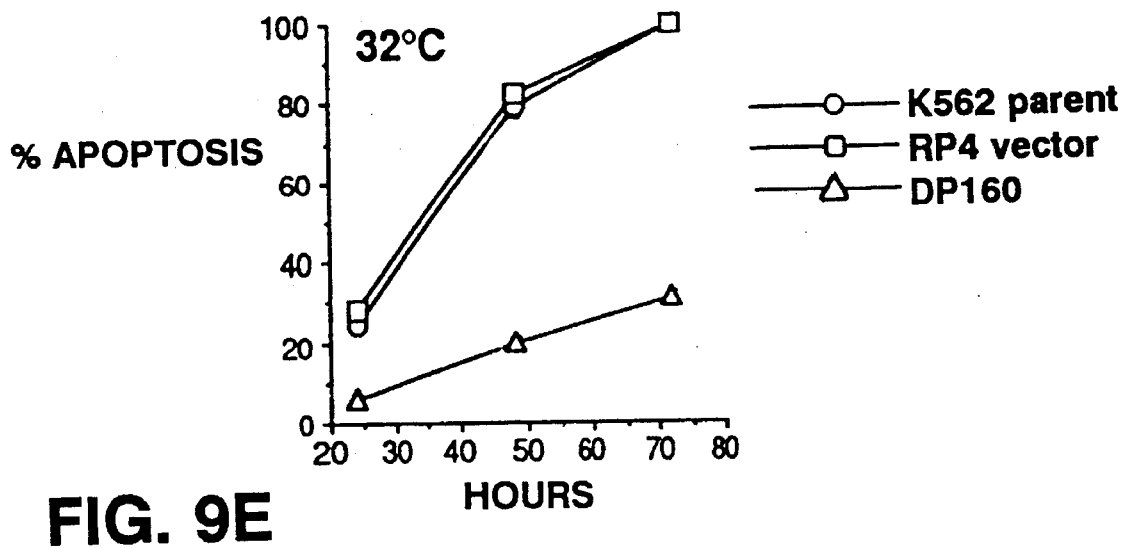
Figure 9F:
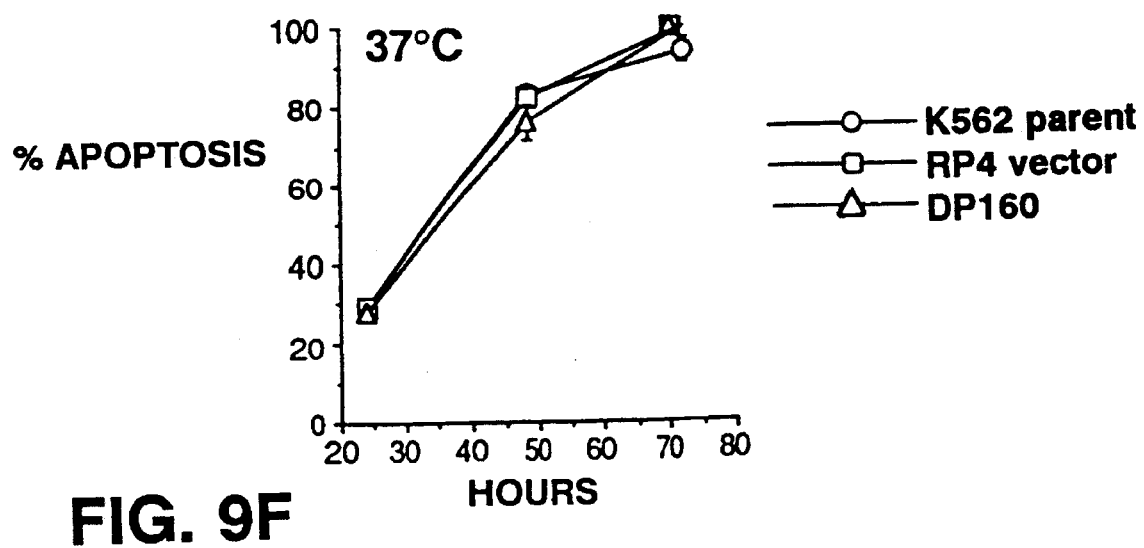

As shown in FIG. 9, all three cell lines were resistant to the effects of VP-16 without pretreatment (FIG. 9A, 9B) or following NS-bcr-abl treatment (FIG. 9C, 9D). When cells were pretreated with AS-bcr-abl and cultured at 37° C. with etoposide, all three lines underwent extensive apoptosis (FIG. 9F). At 32° C., however, the cells expressing v-Abl$^{ts}$ were resistant to the effect of VP-16 while the other lines were not (FIG. 9E). Similar results were seen for serum deprived cells. Since the presence of v-Abl reversed the apoptotic effects caused by administering AS-bcr-abl, the effectiveness of the antisense oligonucleotide in enhancing apoptosis through the targeting and down-regulation of bcr-abl expression was confirmed. The identity of the bcr-abl gene as an anti-apoptosis gene was also confirmed.

EXAMPLE 5

Antisense Induced Apoptosis in Peripheral Blood Cells From CML Patients

Granulocytes were isolated from the peripheral blood of two CML patients using dextran sedimentation and Ficoll Hypaque gradient separation (Weedie, et al., *Leuk. Res.* 14:761, 1990). Cells were counted and seeded in RPMI 1640 medium in the absence of fetal calf serum plus either AS-bcr-abl (10 μM), NS-bcr-abl (10 μM) or no treatment for 0, 10, 20, and 30 hours. Cells were then aspirated and 10⁵ cells were cytospun at 200 rpm onto a glass microscope slide in a Shandon centrifuge. Slides were allowed to air dry and attached cells stained with haematoxylin and eosin for microscopic analysis. Apoptosis was assessed by morphological criteria using cell shrinkage, nuclear condensation/fragmentation as markers for apoptosis (Martin, et al., *Clin. Exp. Immunol.* 79: 448, 1990).

Figure 10A:
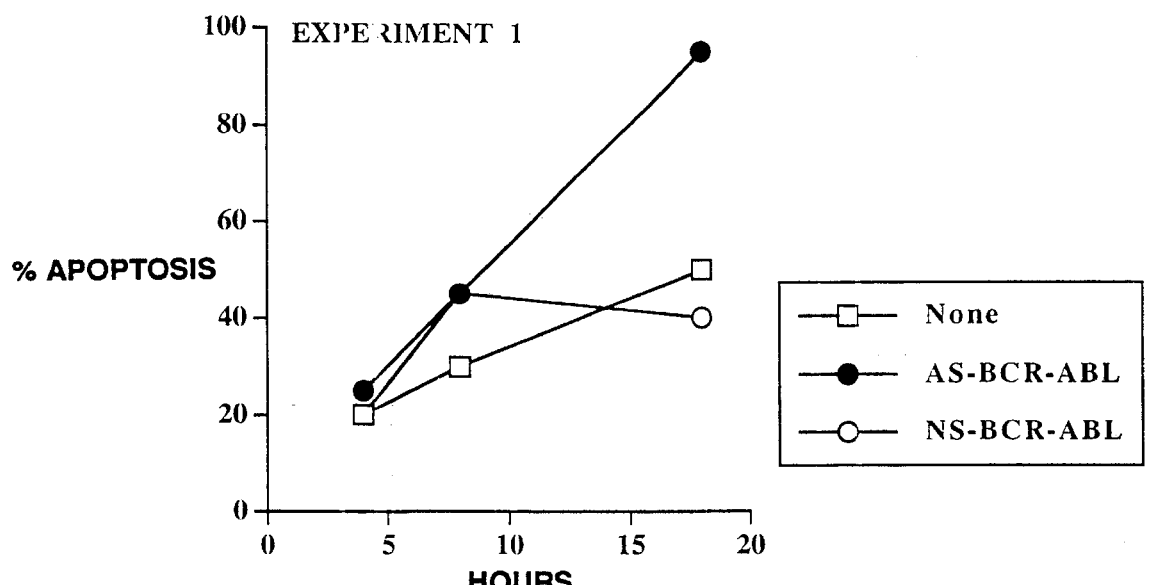
FIG. 10 shows the effect of treatment of peripheral blood cells from CML patients, in the absence of fetal calf serum, plus either AS-bcr-abl (10 μM), NS-bcr-abl (10 μM) or no treatment for 0, 10, 20, and 30 hours.
Figure 10B:
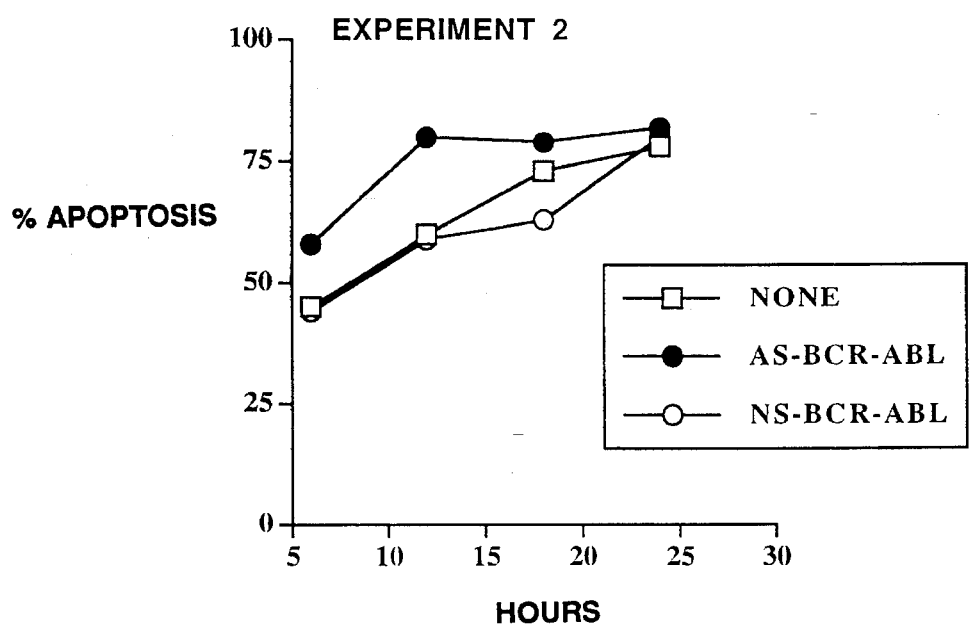

The results are shown in FIG. 10 as hours and percent apoptosis for two different patients. The antisense treatment was highly effective in inducing apoptosis in the first patient (Experiment 1) and moderately effective in the second patient (Experiment 2), as compared to cells treated with either nonsense oligonucleotides or not treated at all, particularly at the 10–20 hour time point (see FIG. 10).

The foregoing is meant to illustrate, but not to limit, the scope of the invention. Indeed, those of ordinary skill in the art can readily envision and produce further embodiments, based on the teachings herein, without undue experimentation.

15
Sequence ID Listing

SEQ ID NO: 1 is the nucleotide sequence of the translation start site of bcr in bcr-abl.

SEQ ID NO: 2 is the nucleotide sequence of the translation start site of abl in bcr-abl.

SEQ ID NO: 3 is the nucleotide sequence of an antisense oligonucleotide complementary to the sense nucleic acid sequence of the translation start site of bcr-abl.

16

SEQ ID NO: 4 is the nucleotide sequence of an antisense oligonucleotide complementary to the sense nucleic acid sequence of the translation start site of abl in bcr-abl.

SEQ ID NO's: 5 and 6 are nucleotide sequences for nonsense oligonucleotides for bcr-abl.

---

We claim:

1. An antisense oligonucleotide having the nucleotide sequence 5'-GCCCACCGGGTCCACCAT-3' (SEQ ID NO:3).

2. The antisense oligonucleotide of claim 1 which is a DNA sequence.

3. The antisense oligonucleotide of claim 1 which is chemically modified.

4. The antisense oligonucleotide of claim 3 which comprises at least one methylphosphonate or phosphorothioate internucleotide linkage.

5. A method for inducing death in a cell having a gene encoding the bcr-abl polypeptide comprising the steps of:

a) administering to the cell in vitro an antisense oligonucleotide having the nucleotide sequence selected from the group consisting of 5'-GCCCACCGGGTCCACCAT-3' (SEQ ID NO:3) and 5'-TACTGGCCGCTGAAGGGC-3' (SEQ ID NO:4) in an amount sufficient to inhibit the expression of the bcr-abl gene; and b) exposing the cell to a chemical or physical means for inducing apoptosis.

6. The method of claim 5, wherein the antisense oligonucleotide is DNA.

7. The method of claim 5 wherein the antisense oligonucleotide is chemically modified.

8. The method of claim 7 wherein the antisense oligonucleotide comprises at least one methylphosphonate or phosphorothioate internucleotide linkage.

9. The method of claim 5, wherein the cell is a chronic myelogenous leukemia cell having a translocated bcr-abl gene.

10. The method of claim 5, wherein the means for inducing apoptosis comprises exposing the cells to a chemotherapeutic apoptotic agent.

11. The method of claim 10, wherein the chemotherapeutic apoptotic agent is selected from the group consisting of actinomycin D, etoposide, cycloheximide, VM-26, and camptothecin.

12. The method of claim 5, wherein the means for inducing apoptosis is a physical treatment.

13. The method of claim 12, wherein the physical treatment is selected from the group consisting of γ-radiation, ultraviolet light, heat shock and cold shock.

14. A method of identifying an agent which induces apoptosis in a cell having a gene encoding the bcr-abl polypeptide comprising the steps of:

a) contacting the cell in vitro with an antisense oligonucleotide having the nucleotide sequence selected from the group consisting of 5'-GCCCACCGGGTC-CACCAT-3' (SEQ ID NO:3) and 5'-TACTGGCCGCT-GAAGGGC-3' (SEQ ID NO:4) in an amount sufficient to inhibit the expression of the bcr-abl gene;

b) contacting the cell with a putative apoptotic agent; and c) observing the effect on the cell.

* * * * *